United States Patent [19]

Täger

[11] Patent Number: 5,021,063
[45] Date of Patent: Jun. 4, 1991

[54] JOINT SOCKET MEMBER FOR A JOINT PROSTHESIS

[75] Inventor: Karl H. Täger, Gauting, Fed. Rep. of Germany

[73] Assignee: Howmedica, Gmbh, Schonkirchen, Fed. Rep. of Germany

[21] Appl. No.: 310,119

[22] Filed: Feb. 9, 1989

[30] Foreign Application Priority Data

Feb. 11, 1988 [DE] Fed. Rep. of Germany ....... 3804239

[51] Int. Cl.$^5$ ................................................ A61F 2/34
[52] U.S. Cl. ......................................... 623/23; 623/18; 623/22
[58] Field of Search .................... 623/16, 18, 22, 23

[56] References Cited

U.S. PATENT DOCUMENTS

| 3,584,318 | 1/1966 | Scales et al. | 623/22 |
| 4,065,817 | 1/1978 | Branemark et al. | 623/22 |
| 4,495,393 | 6/1986 | Annapliotis et al. | 623/22 |
| 4,718,914 | 1/1988 | Frey et al. | 623/22 |
| 4,865,604 | 9/1989 | Rogozinski | 623/23 |

FOREIGN PATENT DOCUMENTS

| 0214885 | 3/1987 | European Pat. Off. | 623/22 |
| 2933271 | 3/1981 | Fed. Rep. of Germany | 623/22 |
| 2154141 | 9/1985 | United Kingdom | 623/66 |

Primary Examiner—David J. Isabella
Attorney, Agent, or Firm—William G. Rhines

[57] ABSTRACT

A joint socket member for a joint prosthesis, in particular a hip joint socket member of a hip joint endoprosthesis in which, in accordance with the invention, the cup element is formed from preferably two cup portions, disposed at least in two cup planes arranged radially at a spacing with a free intermediate space relative to each other, wherein openings are provided at least in the cup portion which is towards the bone, the number, distribution, shape and size of the openings, during the operation, permitting the introduction and secure holding of spongiosa or loose bone substance into the intermediate space and thereafter ensuring growth thereinto of new strong bone substance.

15 Claims, 2 Drawing Sheets

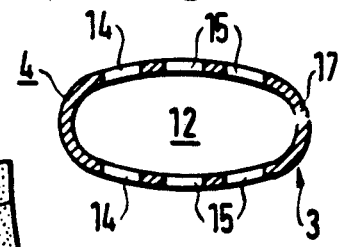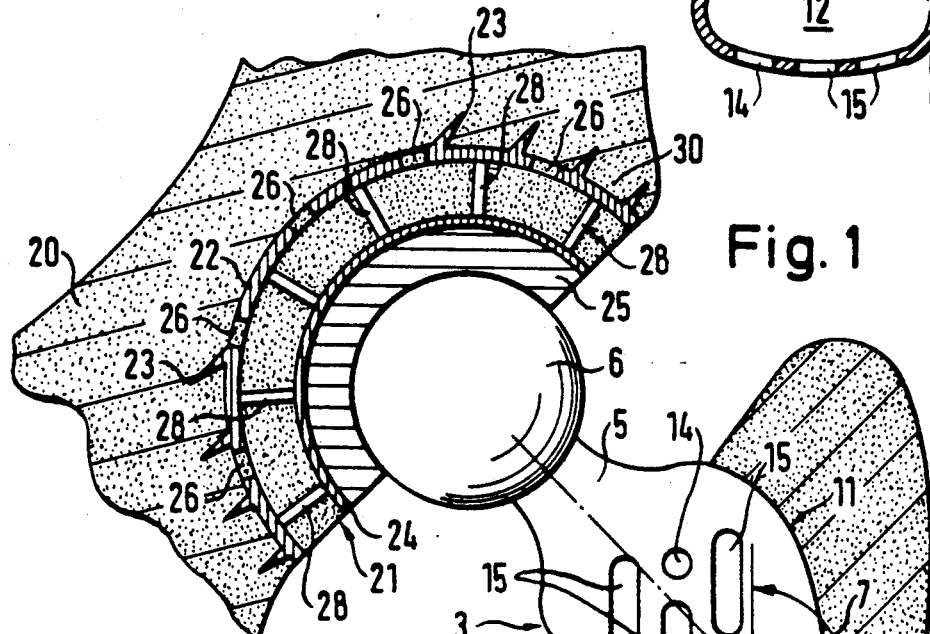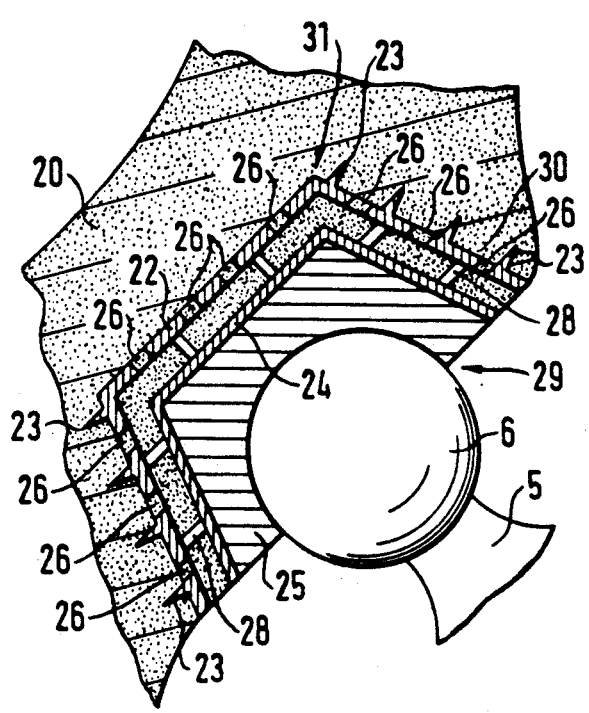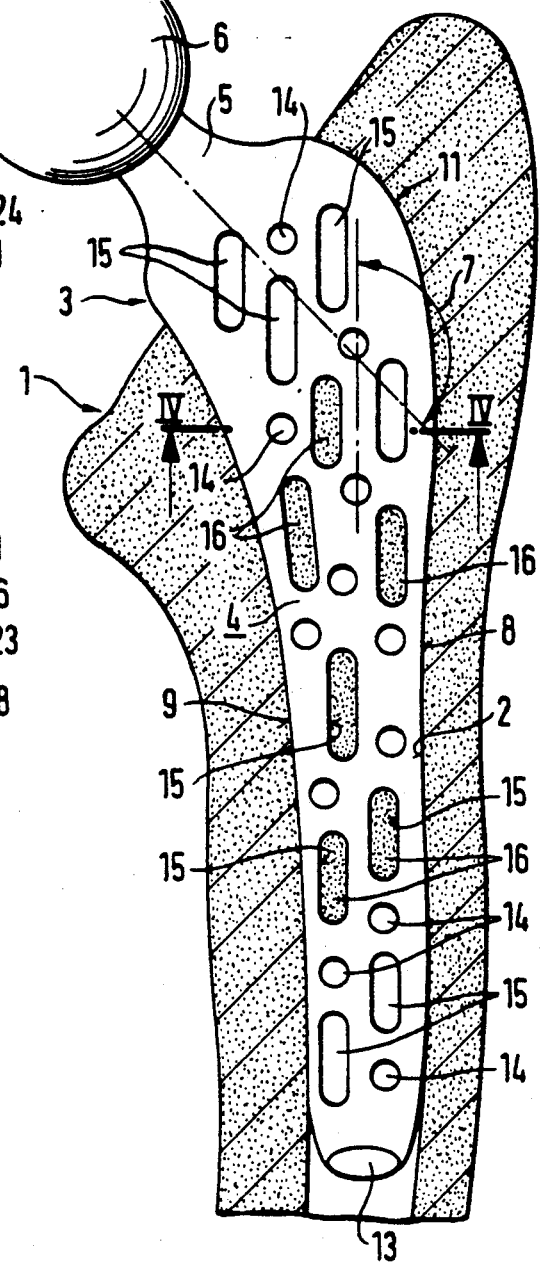

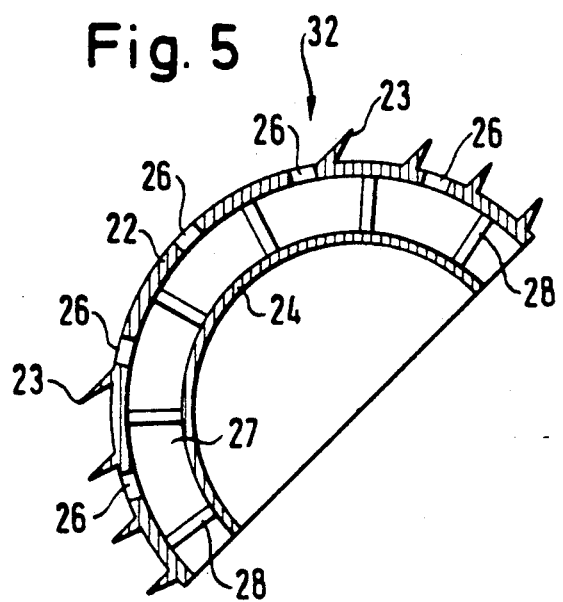
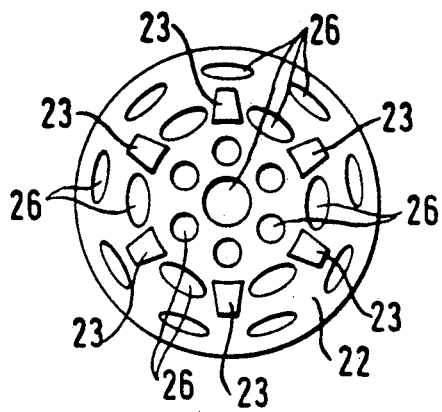
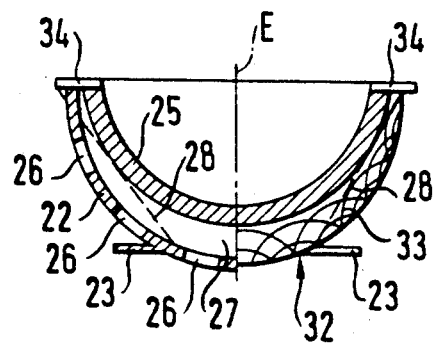

JOINT SOCKET MEMBER FOR A JOINT PROSTHESIS

The invention relates to a joint socket member for a joint prosthesis, in particular a hip joint socket member of a hip joint endoprosthesis with a cup or shell element which is fixed in the bone and which on its joint side has a recess which is of a cup-like, for example hemispherical configuration, for accommodating a sliding socket or an inlay for a joint head.

The fixed insertion of a joint socket member is predominantly effected by screwing the socket body portion into the bone substance by means of a self-tapping screwthread of which for example a plurality of screwthread flight portions project radially laterally from the socket body portion.

The object of the present invention is to strengthen the fixing of the prosthesis to the bone and also to provide for easier fitting of the prosthesis during the operation and quicker and secure healing.

Accordingly, in a joint prosthesis of the kind set forth in the opening part of this specification, the invention is characterised in particular by the features set forth in claim 1.

In accordance therewith, the components of the prosthesis according to the invention, which are to be secured to and in the bone, are of a structure into which on the one hand loose bone substance can be introduced during the operation, without moving out in the subsequent manipulation phase, and by means of which on the other hand the interior of the prosthesis can be anchored with an increased anchoring force to the adjoining parts of the bone by way of a bridge configuration which is of a multiply branched or network-like system.

Preferably, in accordance with the invention, support means for supporting the two cup planes relative to each other and which extend radially or transversely between the two cup portions are provided as set forth in claim 2. The support means therefore carry the elements, which have grown into the bone, of the cup portion which is towards the bone.

Although the openings can be of any desired cross-sectional shape, round or elongate holes are thought to be the most advantageous from the production point of view.

In that connection, the arrangement of the openings as recited in claim 5 can be of especial advantage, wherein the arrangement may involve a particular orientation of the openings, including in regard to their form, such orientation being optimised for example in regard to strength.

By virtue of the reinforced growth interlinking between the prosthesis and the bone, which is achieved with the invention, the size and number of the surface portions or flight portions of the self-tapping screwthread can also be reduced and the work involved in the operation can be improved.

A preferred construction is set forth by virtue of the combination of features recited in claim 6.

In accordance with claims 7 and 8, the cup element may be of a different external shape, while the arrangement of the two cup portions may specifically be as set forth in claim 9.

Material which has been found to be tissue-friendly, in particular highly alloyed metal such as titanium, yitallium etc can be used as the material for the cup element. The inlay or sliding cup which is disposed in the cup element may be made of a high density polyethylene of a wall thickness of about 5 mm although in many cases that sliding cup may also consist of metal.

It has been found that the bone substance which is introduced can be both natural bone tissue or chip material and bone tissue or chip material which is foreign to the body (preserved in a bank).

The invention provides that endoprosthesis of that kind are provided in a form which is substantially open towards the body so that besides rapid growth interlinking, the invention also provides an improvement in subsequent natural supply to the grown bone regions.

In a particularly preferred form the joint socket may also be of a simplified construction as set forth in claim 10 while as set forth in claims 11 to 14 further embodiments which save on material and which are of a compact construction are advantageous. In that case also the radial thickness of the intermediate space or the thickness of the mesh network material is between about 5 and 10 mm.

In particular it is possible to use a larger sliding socket diameter which those constructions. An increase in the joint ball diameter, which is also possible in that construction, reduces the forces applied to the thigh member, in particular also the forces which act with a lever-like action, so that the combination set forth in claim 16 affords synergistic advantages.

Making the sliding socket from metal (titanium etc), which is preferred in accordance with the invention, further saves on the amount of space required for installation, while at the same time completely eliminating wear phenomena.

Although thigh members of hip joint endoprosthesis with a hollow internal space are known, as well as the holes connecting the outside to the internal space (German laid-open application (DE-OS) No 28 51 598.2), difficulties are still encountered in regard to optimising the external profile of the shank portion, which is advantageous in regard to a tight play-free fit, the cross-sectional structure of the shank portion, which ensures optimum stability and strength, the holes provided therein, in regard to nature, size, and distribution or arrangement thereof, and a construction or overall form of the shank portion, which can be produced economically.

In the case of a known shank portion which is made entirely from comparatively thin sheet metal of a constant gauge, the aim to be attained is evidently that the hollow shank and the nature and distribution of the holes, in regard to their longitudinal or bending stiffness, are adapted to each other and to the surrounding bone region, that is to say they do not have any weak points (European patent No 0 065 481).

Providing holes in thin flexible sheet metal involves the risk of the material tearing due to fatigue phenomena, for example in the upper curved shank portion. In particular a thin-gauge shank portion of that kind, which is of a curved configuration in itself, is only comparatively heavy and difficult to produce and in addition can only be connected with its head portion to the joint ball attachment by an expensive operation and in an insecure fashion. Moreover, excessively large cross-sectional configurations in respect to the holes and the internal space are not suitable for holding the introduced bone tissue, in such a way that the arrangement can withstand handling, during the operation.

One construction of the thin sheet metal shank wall, of rectangular cross-section, endangers or does not provide a fixing effect in the femur.

Accordingly the invention also covers a thigh member which in particular can be used jointly with the above-indicated joint socket member for a hip joint endoprosthesis, the shank of the thigh member having an internal space and openings communicating therewith in its wall, and is constructed in accordance with the invention as set forth by the combination of features recited in claim 15. The fact that the shank is also constructed in the form of a cast member, in accordance with the invention, means that the shank is substantially stiffer so that on the one hand there are no problems in regard to strength while on the other hand the hold of the loosely introduced bone substance is improved, and at the same time there are no holding problems, by virtue of an external profile which is fully adapted on all sides to the marrow canal. In particular such a thigh member can also be produced at substantially lower cost.

The invention is described in greater detail hereinafter by means of embodiments given by way of example. In the drawings:

FIGS. 1 and 2 are diagrammatic views in section of a hip joint endoprosthesis, as viewed from the front side, FIG. 3 is a plan view, as seen from the bone substance, of a part of the cup element according to the invention.

FIG. 4 is a view in cross-section taken along line IV—IV in FIG. 1,

FIG. 5 is a diagrammatic view in cross-section through a cup element according to the invention, and FIG. 6A and 6B shows views in cross-section illustrated on two sides of a central plane E, of respective further embodiments of the cup element according to the invention.

Referring to FIG. 1, the shank 4 of a thigh member 3 of an artificial hip joint is introduced into the marrow canal 2 at the hip end 1 of a thigh bone. On a tapering neck portion 5, the shank 4 of the thigh member 3 carries a joint ball 3, the angle between the longitudinal axis of the shank 4 and the neck portion 5, as indicated at 7, being about 135°.

The shank 4 has a lateral side 8 and a medial side 9 and, on its frontal and dorsal sides has openings which may be provided in different shapes, sizes, numbers and distribution, and which communicate with an internal space or cavity 12 provided in the interior of the shank 4. The manner in which the openings are provided (for example round openings 14 and elongate openings 15) ensures not only the introduction of bone substance or corresponding tissue 16, which is natural to the body or foreign to the body, into the hollow internal space 12, but it also ensures that it is held in place during the operation of fitting the prosthesis, which involves forceful movements and also blows and shocks.

For that purpose also the shank 4 is made in the form of a cast component, for example from tantalum, thereby producing a comparatively stiff cast wall 17 which permits additional stiffening thicknesses in the transitional portions of the shape, for example also around the opening 13 in the distal end of the shank.

Fixed in the hip bone 20 is an endoprosthesis socket 21 which with its shell or cup element 32 may be of different shapes, as shown for example in FIGS. 1 and 2. As shown in FIG. 1, it can be in the form of hemispherical cups or truncated hemispherical cups, while in FIG. 2 it is shown in the form of a frustoconical component 29.

As shown in FIGS. 1, 2 and 5, the cup element 32 has a cup portion 22 (inner cup) on the bone side and a cup portion 24 (outer cup) on the socket side. Provided on the cup portion 24 are the flights of a self-tapping screwthread 23 with which the socket is screwed into the soft pelvic bone region 30, by applying a force thereto.

Support and spacer pegs 28 or connecting members are provided in the intermediate space 27.

Prior to fitting, bone substance is also introduced into the intermediate space 27 through openings 26 or corresponding perforations; the introduced bone substance subsequently grows together with the hip bone 20 and anchors the joint socket 21 firmly in the hip bone 20, by means of bone bridge configurations or bone growth portions.

As shown in FIG. 3, the openings 26 are distributed over the surface of the cup portion 22 on the bone side, from which the flights of the screwthread 23 also project outwardly.

The actual joint sliding socket 25 is introduced into the concave hollow surface of the cup portion 24 on the socket side (outer cup), more specifically by being secured to the edge region of the cup portion 22 in which the joint ball 6 is movable.

In the particular embodiments shown in FIG. 6A, the cup portion 24 of the cup element 22, which is on the socket side, can also be formed by the outside of the joint sliding socket 25 in which case the bone substance 16 can be introduced into the intermediate space 27 in an even simpler fashion and, after healing is completed, bone substance which is natural to the body supports the joint sliding socket 25. In the construction shown in FIG. 6 the support and spacer pegs 28 may extend in the form of strut means between the possibly stiffened edge region 34 of the cup portion 22 and the bottom thereof. After healing, same also withstand torsional forces.

In the specific embodiment shown in FIG. 6B, the cup portion 22 on the bone side is substantially reduced to a mesh network arrangement 33 which, carried by the plane of the cup portion 22, extends from a mesh construction into the intermediate space 27 or can also fill same.

The mesh elements may be strong metal wires or bands or strips around which the bone substance grows, thereby providing for shallow anchoring of the socket over the thickness of the intermediate space 27.

I claim:

1. A prosthetic joint socket member having a cup element which is configured and dimensioned to be affixed to the bone and defines a cup-shaped recess for accommodating a bearing element; said cup element comprising a hollow outer shell which is adapted to be affixed to the bone, and an inner shell that forms said recess, said inner shell and said outer shell being spaced radially from each other at a predetermined distance to define an intermediate space therebetween, wherein at least said outer shell has openings to permit loose bone material to be introduced into and held in said intermediate space during surgical emplacement of the member so as to enhance the growth of new bone tissue into said intermediate space.

2. A joint socket member as set forth in claim 1 characterized in that a plurality of spacing pegs extend between and interconnect the inner and the outer shell.

3. A joint socket member as set forth in claim 1 characterized in that the openings are round.

4. A joint socket member as set forth in claim 1 characterized in that the openings are elongated.

5. A joint socket member as set forth in claim 1 characterized in that the bone engaging surface of the outer shell has self-tapping screwthreads thereon.

6. A joint socket member as set forth in claim 1 characterized in that said shells are in the form of segments of spheres arranged one within the other.

7. A joint socket member as set forth in claim 1 characterized in that said shells are frustoconical in shape and are arranged one within the other.

8. A joint socket member as set forth in claim 1 characterized in that the outer surfaces of said shells are substantially parallel with respect to each other.

9. A joint socket member as set forth in claim 1 characterized in that support pegs are arranged to extend between the region of said cup element which defines the opening into said cup-shaped bearing element receiving recess and the interior of said intermediate space, which region has been structurally reinforced to impart added stiffness to it against flexure.

10. A joint socket member as set forth in claim 1 characterized in that said outer shell is a porous mesh comprising crossed filaments wherein the filaments are firmly connected at points of intersection.

11. A joint socket member as set forth in claim 10 characterized in that support pegs are provided as strut means which extend between the exposed edge of said inner shell and the inner regions of the mesh which forms said outer shell.

12. A joint socket member as set forth in claim 11 characterized in that the bone engaging surface of the outer shell has self-tapping screw threads thereon at locations where filaments of said mesh connect.

13. A joint endoprosthesis which is characterized in that
it has a cup element which is configured and dimensioned to be affixed to the bone and defines a cup-shaped recess for accommodating a bearing element; said cup element comprising a hollow outer shell which is adapted to be affixed to the bone, and an inner shell that forms said recess, said inner shell and said outer shell being spaced radially from each other at a predetermined distance to define an intermediate space therebetween, wherein at least said outer shell has openings to permit loose bone material to be introduced into and held in said intermediate space during surgical emplacement of the member so as to enhance the growth of new bone tissue into said intermediate space, and that it has a limb member that has a shank and is adapted for one of its ends to be positioned within said cup-shaped recess, which member is further characterized in that it has a cavity internal of its ends and sidewalls, and openings extending between the exterior surface of the shank and said internal cavity, at least some of which are located in at least one among the anterior and posterior sides of the shank: the configuration and size of those openings and said internal space being adapted to permit spongiosa or loose bone substance to be imbedded into and held in said internal space during surgical emplacement of said member, it comprises a cast component having a comparatively thick wall, and its outside profile is closely adapted to the internal profile of the marrow canal with which it is to be associated.

14. A joint socket member as set forth in claim 1 characterized in that the socket member is so configured structurally as to adapt it for use as a hip joint socket member of a hip joint endoprosthesis.

15. A hip joint endoprosthesis having a cup element which is fixed to the bone and which, on its joint side, has a recess which is of cup shaped configuration for accommodating a bearing insert for the joint and a thigh member having an internal space in its shank and openings between the exterior surface of its shank and said internal space, characterized in that the cup element is made from two cup-shaped portions disposed one inside the other that are spaced radially from each other to define a free intermediate space therebetween, and that openings are provided at least in the outermost cup shaped portion and on at least one among the anterior and posterior sides of the shank, said openings being configured and located so that loose bone substance placed in the intermediate space and the hollow internal space during surgical emplacement of the endoprosthesis may grow into new bone substance.

* * * * *